(12) United States Patent
Weese

(10) Patent No.: US 7,925,327 B2
(45) Date of Patent: Apr. 12, 2011

(54) APPARATUS AND METHOD FOR ASSISTING THE NAVIGATION OF A CATHETER IN A VESSEL

(75) Inventor: Juergen Weese, Aachen (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 1067 days.

(21) Appl. No.: 10/536,843

(22) PCT Filed: Nov. 27, 2003

(86) PCT No.: PCT/IB03/05442
§ 371 (c)(1),
(2), (4) Date: May 31, 2005

(87) PCT Pub. No.: WO2004/051579
PCT Pub. Date: Jun. 17, 2004

(65) Prior Publication Data
US 2005/0288577 A1 Dec. 29, 2005

(30) Foreign Application Priority Data
Dec. 4, 2002 (EP) .................................... 02102682

(51) Int. Cl.
*A61B 5/05* (2006.01)
(52) U.S. Cl. ........................................ 600/424; 606/130
(58) Field of Classification Search .......... 600/424–439, 600/407–410, 473–476; 606/130
See application file for complete search history.

(56) References Cited

U.S. PATENT DOCUMENTS

| 6,148,095 | A | 11/2000 | Prause et al. | |
|---|---|---|---|---|
| 2002/0077546 | A1 | 6/2002 | Beckmann et al. | |
| 2003/0103212 | A1* | 6/2003 | Westphal et al. | 356/479 |
| 2003/0199767 | A1* | 10/2003 | Cespedes et al. | 600/473 |
| 2003/0229286 | A1* | 12/2003 | Lenker | 600/462 |
| 2003/0236443 | A1* | 12/2003 | Cespedes et al. | 600/29 |
| 2004/0097805 | A1* | 5/2004 | Verard et al. | 600/428 |
| 2005/0014995 | A1* | 1/2005 | Amundson et al. | 600/105 |
| 2005/0107688 | A1* | 5/2005 | Strommer | 600/424 |
| 2006/0058647 | A1* | 3/2006 | Strommer et al. | 600/434 |
| 2007/0287901 | A1* | 12/2007 | Strommer et al. | 600/407 |

FOREIGN PATENT DOCUMENTS

EP  0885594  12/1998

OTHER PUBLICATIONS

"Towards Real-Time Multi Modality 3-D Medical Image Registration" to Weese et al. 2001.*

* cited by examiner

*Primary Examiner* — Long V Le
*Assistant Examiner* — Sanjay Cattungal

(57) ABSTRACT

The invention relates to the assistance of the navigation of a catheter (1) in a vessel (2). A sequence of cross-sectional images of the portion of the vessel that is of interest is first obtained with the help of an intravascular ultrasound (IVUS) probe (3) and stored as a roadmap of the vessel. A cross-sectional image (10) that is obtained at the current position of the IVUS probe (3) can then be sorted to the position on the roadmap that is the best fit. A model (3') of the probe, and a model (11') of the instrument (a stent (11), for example) coupled to the probe, can be shown on a display (6) at the corresponding position on the roadmap.

25 Claims, 1 Drawing Sheet

APPARATUS AND METHOD FOR ASSISTING THE NAVIGATION OF A CATHETER IN A VESSEL

The invention relates to an apparatus and method for assisting the navigation of, for example, a catheter in a vessel.

In intravascular medical procedures, an instrument carried at the tip of a catheter is fed along the path followed by a vessel to an operative site from a point in the vascular system that is easily accessible from outside. The desired diagnostic or therapeutic procedures can then be performed with the instrument at the operative site. A stent, for example, may be placed at the site of a stenosis in an artery or a coronary vessel to widen the constriction in the vessel. For such procedures to be successful, it is important to be able to navigate the instrument reliably in the vessel and to be able to perform the desired procedures at exactly the point aimed for. To assist the guidance of a catheter, the procedure is therefore usually observed by means of X-ray fluoroscopy, a clear representation of the vessels being obtained by the injection of a contrast medium. However, because of the stress involved on the patient, the amount of contrast medium that can be injected is limited and without a contrast medium the vessels are difficult or quite impossible to see in the X-ray images. A further disadvantage is the exposure of the patient to radiation that the X-ray imaging involves and the restriction of what is depicted to regions in which there is blood flowing. The walls of vessels, deposits on the walls of vessels, and surrounding tissue on the other hand are not very accurately imaged.

To improve the three-dimensional representation of vessels of complex shape, it is known from U.S. Pat. No. 6,148,095 for angiographic projected images taken from two different directions to be combined with intravascular ultrasound (IVUS) images. The method is very costly and complicated and, to allow the current position of a catheter to be determined, calls for X-ray images, which involves corresponding exposure of the patient to radiation.

Against this background, it is an object of the present invention to provide an apparatus and method for assisting navigation in a vessel, which apparatus and method, while reducing the stress and radiation exposure caused by examination, allow an instrument, such as the tip of a catheter for example, to be more exactly positioned.

This object is achieved by an apparatus having the features given in claim 1 and by a method having the features given in claim 5. Advantageous embodiments are contained in the dependent claims.

The apparatus according to the invention serves to assist navigation in a vessel. What is meant by a "vessel" in this case is primarily a blood vessel in a volume of biological body matter. The invention is not, however, limited to this and can be applied in principle to navigation in vessels or ducts in a more general sense (such as, for example, ducts or passages in the structure of a machine). The apparatus comprises the following elements:

a) A sensor probe for acquiring local images that characterize the vessel at the point where the particular local image is made, which sensor probe can be moved along the vessel. The term "image" is to be understood in a wide sense in this connection and covers measurement data of all kinds that reflects the characteristic local attributes of the vessel (e.g. the local electrical resistance in the vessel). Examples of local images are explained below in connection with preferred embodiments of the invention.

b) A memory for storing a sequence of local images that are obtained in the course of the movement as mentioned above of the sensor probe along the vessel. A graphic representation of this sequence is also referred to below as a "roadmap" of the vessel.

c) A data-processing unit that is arranged to sort (at least) one further local image of the vessel into the sequence of local images that is stored in the memory in step b). The further local image is preferably obtained by the said sensor probe in this case and is thus of the same type as the local images that have already been stored in the sequence. It is, however, also conceivable for the further local image to be obtained by a different device or in a different way.

With the apparatus described and its sensor probe, it is possible to navigate in a vessel. For this purpose, a roadmap of a portion of the vessel is first obtained in steps a) and b) and stored. In the course of subsequent movement of the sensor probe or another instrument to obtain local images, "further" local images obtained at the point currently reached can then be assigned to a point on the roadmap held in store, i.e. the position of the sensor probe or the instrument can be identified on the roadmap.

The sensor probe is preferably an intravascular ultrasound system (IVUS). Cross-sectional images of the vessel (images perpendicular to the axis of the vessel) can be obtained with an IVUS, with the cross-sections showing characteristic attributes of the vessel (shape and diameter of the lumen, thickness of the walls of the vessel, deposits on the walls of the vessel, surrounding tissue, etc.) at the imaging point. As a rule, there is a continuous variation in these attributes along the vessel, and they are therefore suitable for identifying or determining the parameters of positions along the path followed by the vessel. Another advantage of an IVUS is that it can be used to obtain images without the patient being exposed to radiation. Also, the cross-sectional images produced by the IVUS are suitable for directly identifying and examining a constriction of the vessel (a stenosis). An IVUS is therefore already being used anyway in many examinations performed by catheter.

A system for performing optical coherence tomography (OCT) also constitutes a suitable type of sensor probe because the advantages it has are similar to those of an IVUS.

In a further refinement of the invention, it has a means for moving the sensor probe along the vessel at a defined, and preferably constant, speed. A means of this kind can be used to move the sensor probe in a defined way while the latter is making the sequence of local images that are placed in store. The speed of movement of the sensor probe is known and the distance traveled by the sensor probe can be determined at any time from this knowledge and can be represented along a straight scale on a straightened-out roadmap of the vessel. The times at which the local images in the stored sequence were made are known and this knowledge can be used to then assign each local image in the sequence to an associated point on the straightened-out roadmap. What the user of the apparatus obtains in this way is as it were a one-dimensional, true-to-scale reproduction of conditions along the path followed by the vessel.

Another refinement of the invention is characterized in that the apparatus comprises a display for showing the stored sequence of local images, i.e. a "roadmap" of the vessel. The data-processing unit is also arranged to show the current position of the sensor probe, and/or the current position of an instrument that is situated in a known position relative to the sensor probe, on the display in roadmap-form. When the apparatus is used in the context of an examination by catheter, a sequence of local images of the section of the vessel that is of interest may, for example, first be made and shown on the display. In the course of the subsequent diagnostic or therapeutic treatment, the position of the catheter coupled to the sensor probe, or rather of the catheter tip or a guidewire, can then be determined from the position of the sensor probe and shown too on the display to the doctor performing the treatment.

The invention further relates to a method of assisting navigation in a vessel (vessel in the sense explained above), that comprises the following steps:

a) Movement, along the vessel, of a sensor probe for making local images (images in the sense explained above) that characterize the vessel at the point where the particular local image is made.
b) Generation and storage of a sequence of local images by means of the sensor probe during the movement in step a).
c) Sorting of (at least) one further local image of the vessel, which is preferably also made by the sensor probe, into the sequence that is stored step in b).

A method of this kind can be carried out with the apparatus described above, in which case the advantages described there of simple, accurate, low-stress navigation in a vessel by means of a roadmap of the vessel are obtained.

What are suitable for use as local images are in principle all kind of measurement data or sets of measurement data that cover characteristic attributes at a point in the vessel and preferably vary (continuously) along the vessel, thus making them suitable for identifying/giving the parameters of the position in the vessel. What is especially preferable in this connection is the use of intravascular ultrasound images as local images of the vessel. On the one hand these can be obtained with only minimal stress on the patient and on the other they provide valuable information on constrictions in vessels. Intravascular ultrasound images are therefore already being used anyway in many examinations performed by catheter.

In step a) of the method, the movement of the sensor probe preferably takes place at a defined (and preferably constant) speed, while in step b) the generation of local images during the movement takes place at a defined (and preferably constant) rate. The locations of the local images making up the sequence can then be determined and shown to scale on a one-dimensional, straightened-out roadmap of the vessel. If, for example, the movement takes place at a constant speed and the generation of local images takes place at a constant rate, the local images making up the sequence will be equidistant from one another on the roadmap.

There are various possible way in which the sorting of a further local image into the sequence of local images stored previously that is undertaken in step c) may be implemented. Preferably, the sorting is performed by assigning the further local image to a single local image in the sequence, or
to two adjoining local images in the sequence, with the selection of the associated local image(s) in the sequence being made on the basis of a scale of similarity. The similarity between the further local image and the local images making up the sequence (or some of these images) is quantified with the help of the scale of similarity. What is assigned to the further local image is, for example, that local image in the sequence that is most similar, i.e., for which the reading on the scale of similarity is a maximum. The maximum in relation to the sequence in this case may be overall (of all the images in the sequence, the image that is assigned is the one that has the greatest similarity to the further image) or local (only in a portion of the sequence is the image that is assigned the one that has the greatest similarity to the further image). If it is two adjoining local images in the sequence that are to be assigned to the further image, a suitable rule based on the scale of similarity needs to be defined for selecting them. Those two adjoining local images may, for example, be assigned whose degrees of similarity to the further image are a maximum when summed.

In a further refinement of the invention, step c) (sorting of a further local image into the sequence held in store) is performed repeatedly for a series of further images, with the search for a sorted position in the sequence of local images held in store, for an image in this series, beginning in each case at the sorted position that was assigned to the previous image in the series. Initialization of the sorting procedure in this way is found to be advantageous if a series of further local images between which there is a temporal connection is to be sorted into the sequence held in store. This is because, in this case, the position of an image in the series will, as a rule, differ only slightly or not at all from the position of the previous image in the series. The position of the previous image therefore represents a good approximation of the position of the subsequent image in the series, which means that a search that begins with it will be successful more quickly.

In a preferred embodiment of the method, the local images in the sequence held in store are shown on the display, in line with their positions along the vessel, as a roadmap of the vessel. Also, the sorted position in the sequence calculated for the further local image can be superimposed on the same display. The current position of the sensor probe or of an instrument connected thereto can therefore be tracked clearly on the display in relation to the roadmap.

These and other aspects of the invention are apparent from and will be elucidated with reference to the embodiments described hereinafter.

Figure 1:
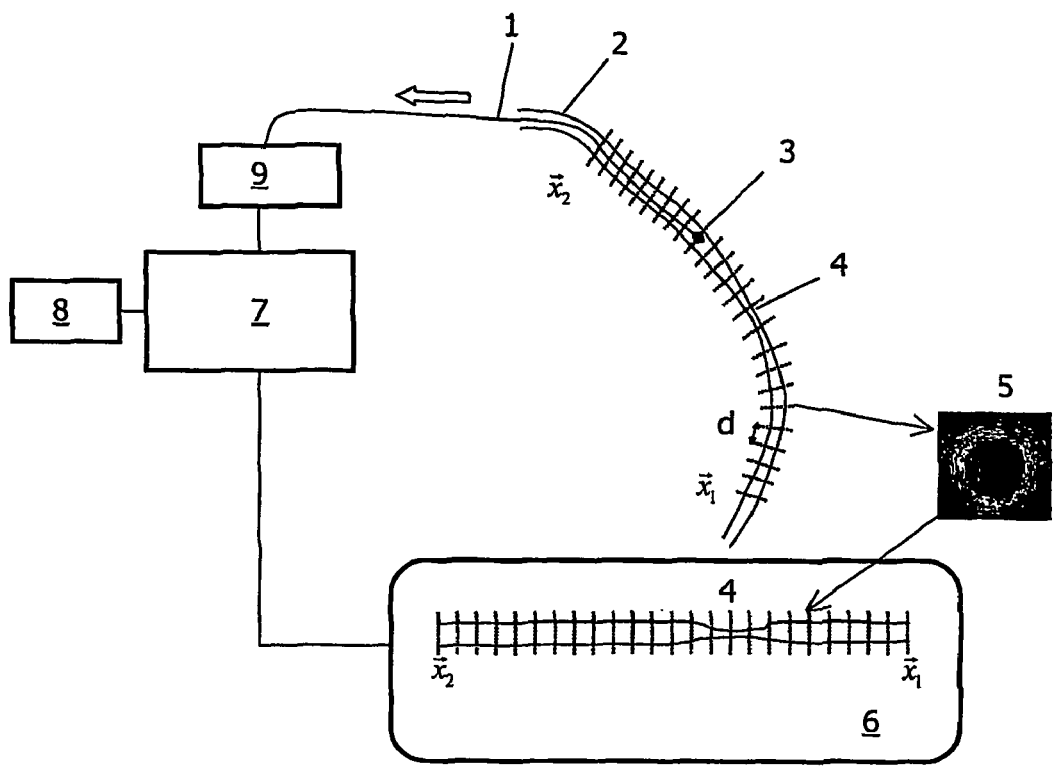
FIG. 1 is a diagrammatic view of the production of a vessel roadmap with the help of an intravascular ultrasound system (IVUS).

The invention is illustrated in the Figures by taking as an example the positioning of a stent 11 for treating a stenosis 4 in a vessel 2 (e.g. a coronary vessel) of a patient. It is important for the successful insertion of a stent that it should be positioned exactly at the stenosis that is to be treated. For this purpose, the stent is usually advanced, at the tip of a catheter 1, along a guidewire while repeated X-ray images are made, accompanied by the injection of a contrast medium, to allow the correct position to be determined. What is disadvantageous about this procedure is the stress on the patient caused by the contrast medium and exposure to radiation caused by the X-ray images.

For this reason, use is made, for a catheter 1 in a vessel 2, of a method of positioning and navigation in which an IVUS probe 3 is employed at the tip of the catheter 1. Ultrasonic cross-sectional images of the vessel 2 can be generated with the IVUS probe 3 at the position occupied by the probe 3, which does not involve any harmful exposure to radiation for the patient. The direct use of an IVUS probe 3 in the positioning of a stent or in some other procedure employing a catheter does, however, come up against the problem that there is generally a considerable distance between the probe 3 and the point at which the instrument (a stent, etc.) acts. Hence, if the IVUS probe 3 is positioned in the center of a stenosis 4, the stent 11 will generally already have been pushed out beyond the stenosis.

To avoid problems of this kind when using an IVUS probe 3, a roadmap of the portion of the vessel 2 that is of interest is first produced in accordance with the invention. The exact position of the stent in relation to the current position of the IVUS probe 3 can then be determined with the help of this roadmap. In this connection, the production of the roadmap will first be explained in detail by reference to FIG. 1.

Shown in FIG. 1 is a portion of a vessel 2 that is of interest, in which there is a stenosis 4 requiring treatment. An IVUS probe 3 has been inserted into the vessel 2 by means of a catheter 1. Beginning from a starting point $\vec{x}_1$, on the further side of the stenosis 4, the IVUS probe is pulled back in the direction of the block arrow to an end point $\vec{x}_2$, preferably at a constant speed, which may, for example, be done by a diagrammatically indicated means 9 outside the patient's body. At the same time, local images 5 are generated at a constant rate by the IVUS probe 3. What is achieved by the combination of a constant speed of pullback and a constant imaging rate is that local cross-sectional images 5 are generated at lengthwise distances d along the vessel 2 that are all the same.

The images 5 generated by the IVUS probe 3 are received by a data-processing unit 7 and are stored in a memory 8. If required, geometrical corrections may be applied to the IVUS images to allow, for example, for the overall configuration of the vessel, which may be known from an existing X-ray image made with contrast medium. Particularly where coronary vessels are being examined, ECG data may also be used to enable IVUS images matched to the cardiac phase to be selected.

The data-processing unit 7 is coupled to a display 6 on which a representation of the sequence of local images 5 that are obtained as the probe 3 is pulled back is shown. The portion of vessel examined is shown straightened out when this is done because, by itself, the IVUS probe 3 does not provide any information on the complex three-dimensional configuration of the vessel. It would, it is true, be possible for the portion of vessel to be shown in three-dimensional form with the help of X-ray images, but this is not necessary for tasks such as the positioning of a stent.

The sequence of local cross-sectional images 5 that is obtained between the starting point $\vec{x}_1$, and the end point $\vec{x}_2$ of the pullback of the probe 3 may be represented in various ways. In the Figures, it is indicated by way of example that the diameters of the vessel 2 calculated from the local images 5 are used to show a (straightened-out) longitudinal section through the vessel. The stenosis 4 can be seen particularly clearly in this "roadmap" of the vessel.

Figure 2:
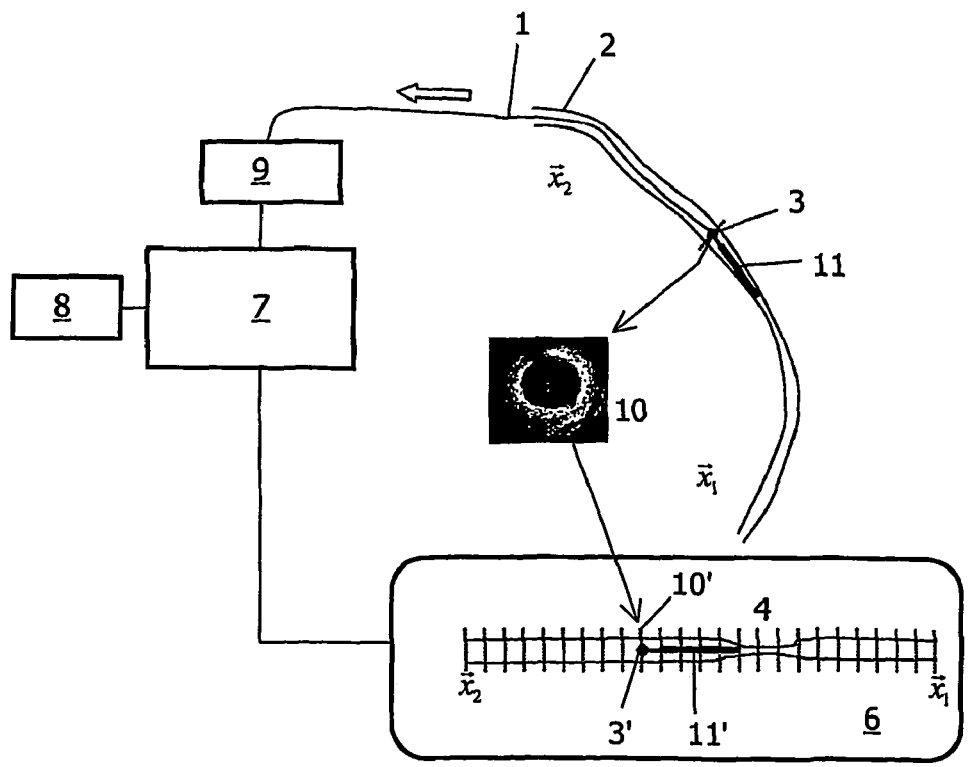
FIG. 2 shows the positioning of a stent in the system shown in FIG. 1.

The use, during the positioning of a stent 11, of the roadmap that is obtained is shown in FIG. 2. The stent 11 is situated in this case on the catheter 1 at a known, constant distance from the IVUS probe 3. Local cross-sectional images 10 are again made with the IVUS probe 3 at the respective points at which the probe 3 is located at the time and are conveyed to the data-processing unit 7. With the help of suitable gray-value based registration techniques (as described, for example, in: D. L. G. Hill et al., Medical Image Registration, Phys. Med. Biol. 46(3), 2001; J. B. A. Maintz, M. A. Viergever, A survey of medical image registration, Med. Imag. Anal. 2(1), 1998; J. Weese et al., Gray-value based registration of CT and MR images by maximization of local correlation, Proc. of MICCAI 1999, LNCS 1679; T. Netsch et al., Towards real-time multi-modality 3D medical image registration, Proc. of ICCV 2001, IEEE Computer Society) that local image 10' that is most similar to the current cross-sectional image 10 is determined in the sequence making up the roadmap. If the roadmap is looked upon as a 3D image (made up of three-dimensional cross-sectional images placed one behind the other), this is equivalent to the registration of a section in a volume.

Advantageously, when the most similar image 10' in the roadmap is being looked for, what is used as a starting value for the comparison of similarities is that image in the roadmap that was assigned to the immediately preceding current cross-sectional image, because, as a rule, the IVUS probe 3 will have moved onward by only a small amount since this assignment was made. By initializing the search in this way, the computing time can thus be reduced and the robustness of the method increased.

The registration of the current cross-sectional image 10 gives the current position of the sensor probe 3 in relation to the roadmap formed by the sequence of earlier cross-sectional images 5 that were obtained as shown in FIG. 1. Because the position of the stent 11 in relation to the probe 3 is known, the current position of the stent 11 on the roadmap is known too. The data-processing unit 7 is therefore able to show on the display 6 both a model 3' of the IVUS probe 3 and a model 11' of the stent 11 at the corresponding position on the roadmap. This gives the doctor a very good check on the actual position of the stent 11, thus enabling him to position the latter in the stenosis 4 with great accuracy.

By using an IVUS probe, accurate and easy positioning of a stent or a similar instrument along the path followed by a vessel can thus be performed with little stress on the patient. Because the method is based on intravascular imaging in this case, no complicated steps have to be taken to compensate for body movement caused by breathing or the beating of the heart.

The invention claimed is:

1. An apparatus for navigation in a vessel, comprising:
a catheter having a sensor probe connected thereto, the sensor probe being configured to move along the vessel, the sensor probe being configured to acquire a series of local images of the vessel at a region of interest as the sensor probe moves along the vessel;
a memory for storing a sequence of the local images that is obtained in the course of the movement of the sensor probe along the vessel; and
a data-processing unit that is configured to sort a further local image of the vessel into the sequence that is stored in the memory, the sorting being based on at least one similarity of at least one characteristic attribute of the vessel as shown within the further local image and one or more of the local images of the sequence.

2. An apparatus as claimed in claim 1, wherein the sensor probe is an intravascular ultrasound system.

3. An apparatus as claimed in claim 1, wherein the sensor probe moves along the vessel at a defined speed.

4. An apparatus as claimed in claim 1, further comprising a display for showing a stored sequence of the local images, wherein at least one of a position of the sensor probe and a position of an instrument that is in a known position relative to the sensor probe is indicated on the display.

5. An apparatus as claimed in claim 1, wherein the local images are cross-sectional images of the vessel.

6. An apparatus as claimed in claim 1, wherein the local images are cross-sectional intravascular ultrasound images of the vessel.

7. A method of navigation in a vessel, comprising:
providing a catheter with a sensor probe;
moving the sensor probe along the vessel, the sensor probe acquiring a series of local images of the vessel at a region of interest as the sensor probe moves along the vessel;

storing a sequence of the local images during the movement of the sensor probe;

sorting a further local image, which is made by the sensor probe, into the sequence based on at least one similarity of at least one characteristic attribute of the vessel as shown within the further local image and one or more of the local images of the sequence; and positioning a medical device coupled to the catheter based at least in part on the sorted further local image.

8. A method as claimed in claim 7, wherein the local images are cross-sectional intravascular ultrasound images of the vessel.

9. A method as claimed in claim 7, wherein the movement of the sensor probe for acquiring the sequence of local images takes place at a defined speed and the generation of local images takes place at a defined rate.

10. A method as claimed in claim 7, wherein the further local image is assigned to one or two adjacent images in the sequence with which the at least one similarity of the further local image is greatest.

11. A method as claimed in claim 7, wherein the sorting of the further local image is performed repeatedly for a series of further local images, with the search for a sorted position in the sequence held in store, for an image in this series, beginning in each case at the sorted position of the previous further local image in the series.

12. A method as claimed in claim 7, wherein the local images in the sequence are shown on a display in line with their positions along the vessel.

13. The method of claim 7, wherein the local images and the further local image are acquired by the sensor probe through performing optical coherence tomography.

14. The apparatus of claim 1, wherein the local images and the further local image are acquired by the sensor probe through performing optical coherence tomography.

15. A method as claimed in claim 7, wherein the local images are cross-sectional images of the vessel.

16. A method of positioning a medical device in a vessel, comprising:

providing a catheter with a sensor probe;

moving the sensor probe along the vessel and acquiring a series of local images of the vessel at a region of interest as the sensor probe moves along the vessel;

storing a sequence of the local images during the movement of the sensor probe;

connecting a medical device to the catheter, the medical device and the sensor probe being separated along the catheter at a known distance;

moving the medical device along the vessel and acquiring a further local image of the vessel at the point where the particular further local image is made;

sorting the further local image into the sequence based on at least one similarity of at least one characteristic attribute of the vessel as shown within the further local image and one or more of the local images of the sequence; and positioning the medical device coupled to the catheter based at least in part on the sorted further local image.

17. The method of claim 16, further comprising moving the sensor probe along the vessel by pulling motion.

18. The method of claim 16, wherein the medical device is a stent.

19. The method of claim 16, further comprising performing geometrical corrections to the local images based on pre-existing images.

20. The method of claim 16, further comprising determining the at least one similarity of at least one characteristic attribute of the as shown within the further local image and the one or more of the local images of the sequence based on gray-value registration.

21. The method of claim 16, wherein the local images and the further local image are acquired using ultrasound imaging.

22. The method of claim 16, wherein the local images and the further local image are acquired using optical coherence tomography.

23. The method of claim 16, wherein the local images are obtained by moving the sensor probe at a constant rate and acquiring the local images at a constant rate.

24. A method as claimed in claim 16, wherein the local images are cross-sectional images of the vessel.

25. A method as claimed in claim 16, wherein the local images are cross-sectional intravascular ultrasound images of the vessel.

* * * * *